United States Patent [19]
Janousch

[11] Patent Number: 6,022,215
[45] Date of Patent: Feb. 8, 2000

[54] METHOD OF PRODUCING AN IMPLANT-SUPPORTED SUPERSTRUCTURE AND ITS SUPPORT FRAME, AND SUPPORT ELEMENT FOR HEAT TREATMENT OF THE SUPERSTRUCTURE AND ITS SUPPORT FRAME

[76] Inventor: Rainer Janousch, Haselburgstrabe 8, D-81545 Munich, Germany

[21] Appl. No.: 08/952,037
[22] PCT Filed: Mar. 5, 1997
[86] PCT No.: PCT/EP97/01101
 § 371 Date: Mar. 5, 1998
 § 102(e) Date: Mar. 5, 1998
[87] PCT Pub. No.: WO97/32538
 PCT Pub. Date: Sep. 12, 1997

[30] Foreign Application Priority Data

Mar. 6, 1997 [DE] Germany ............... 196 08 755

[51] Int. Cl.[7] ............................................. A61C 1/14
[52] U.S. Cl. ........................................................ 433/49
[58] Field of Search ............................ 433/49, 172, 173; 432/258, 259, 261

[56] References Cited

U.S. PATENT DOCUMENTS

| | | |
|---|---|---|
| 3,885,313 | 5/1975 | Kikuchi et al. ................. 433/213 |
| 4,136,449 | 1/1979 | Penrod et al. .................... 433/49 |
| 4,184,840 | 1/1980 | Gamberg et al. ................ 432/258 |
| 4,227,874 | 10/1980 | Nugent ............................ 432/261 |
| 4,634,561 | 1/1987 | DeLuca ............................. 433/34 |
| 5,419,700 | 5/1995 | Sillard ............................. 433/172 |

FOREIGN PATENT DOCUMENTS 0245693  11/1987  European Pat. Off. .
9320774  10/1993  WIPO .

*Primary Examiner*—John J. Wilson
*Attorney, Agent, or Firm*—Knobbe, Martens, Olson & Bear, LLP

[57] ABSTRACT

The invention relates to a method of producing an implant-supported superstructure, with a heat-treatment model being prepared subsequent to the production of a superstructure, which heat-treatment model matches accurately a master model and/or the oral situation of a patient and on which a heat treatment of the superstructure is carried out.

29 Claims, 5 Drawing Sheets

METHOD OF PRODUCING AN IMPLANT-SUPPORTED SUPERSTRUCTURE AND ITS SUPPORT FRAME, AND SUPPORT ELEMENT FOR HEAT TREATMENT OF THE SUPERSTRUCTURE AND ITS SUPPORT FRAME

FIELD OF THE INVENTION

The invention relates to a method ensuring the production of a stress-free implant-supported superstructure and/or its support frame by means of an individual support element as well as by means of an individual support element for a metal frame of a superstructure during a heat treatment step or the firing of ceramic material.

BACKGROUND OF THE INVENTION

For supplying a patient with prosthesis it is known to insert implant bolts into his jawbone, with a superstructure being fitted thereon, which is faced e.g. with ceramic material (having the color of the teeth). The common procedure is to take an impression by means of an individual spoon after having implanted the bolts, which shows the situation in the patient's mouth, in particular the shape of the jawbone, of the mucosae a.s.o. as well as the position of the implanted bolts. For this purpose, transfer jigs are fitted to the implanted bolts in known manner, which are then embedded in the impression of the individual spoon. Subsequently, model implants are screwed into the transfer jigs thus allowing to prepare a master model into which the model implants are embedded in the same manner as the implant bolts are in the patient's jawbone. Using said master model, the superstructure is molded from wax casted in a casting process, using conventional auxiliary elements.

These process steps are known from the state of the art so that a more detailed description thereof can be dispensed with.

The casted raw superstructure is soft and moldable to a certain extent due to the metal alloys used (e.g. gold alloys). The superstructure furthermore shows deformations caused by the cooling and shrinking processes during the casting step, so that generally it will not exactly match the master model. It is known from the state of the art to divide the casted superstructure and solder it in appropriate manner, in order to make it match again. This, however, turned out to be insufficient, as during the subsequent processing of the superstructure and when facing it with facing material, e.g. ceramic material, deformations occur again. It is therefore known from the state of the art that, as a result, the superstructures are to be reworked in order to make them fit. On the one hand, this requires a high expenditure of work in a laboratory, on the other hand it cannot be ensured that the superstructure can be fitted to the implanted bolts of the patient without any problems. In unfavorable cases the superstructure is to be reworked in a dental laboratory or the entire superstructure is to be produced anew.

SUMMARY OF THE INVENTION

The invention is based on the problem of providing a method of producing an implant-supported superstructure which allows the production of fitting superstructures in simple manner and allowing simple handling liable in operation.

The invention is based on the further problem of providing a support element for performing the process, which element is simple and inexpensive in construction and the use of which incurs no difficulties.

Therefore it is the object of the invention to create a method of producing an exactly fitting implant-supported superstructure, wherein the inaccurately shaped superstructure or its support frame is made to fit by means of an individual passivation tray. It is also an object of the invention to construct said support element in a manner that it can be used for the ceramic facing of the superstructure, avoiding distortion of the superstructure from the heat treatment when firing the ceramic material.

According to the invention the problem of the method is solved by producing a heat-treatment model imitating the situation in a patient's mouth reproduced by the master model, with model anchors being inserted into the heat-treatment model in the same manner as the model implants, and by screwing the casted superstructure and/or its support frame to the heat-treatment model, subjecting it to a heat treatment thereafter. Thereby the superstructure and/or the support frame are formed to exactly match the geometry of the heat-treatment model.

According to the invention, the term "superstructure" can comprise the support frame of the superstructure as well as the finished superstructure which is provided with a facing of ceramic material.

The mode of procedure according to the invention distinguishes by a number of considerable advantages. While it was a common measure in the state of the art to divide the casted superstructure mechanically (prior as well as subsequently to facing) and to solder it again, thus making it match the master model, it is now possible according to the invention to ensure the dimensional stability of the superstructure by means of the additional heat treatment. It is preferred that the heat treatment is a stress-relieving anneal treatment. The result is that the superstructure no longer inheres internal stresses possibly leading to fitting inaccuracies during the further treatment or after the insertion into the patient's mouth, thus entailing cracks in the ceramic material. As superstructures are to be produced in an exact manner, e.g. in order to match the shape of still existing teeth of a patient or to ensure exact occlusion, this is of particular importance.

The heat-treatment model according to the invention is identical to the master model, thus reproducing exactly the situation in the patient's mouth. This allows to design the superstructure in a manner that it will fit most accurately by means of the heat treatment.

According to the invention the heat-treatment model can be produced by making use of an individual spoon. Said spoon still exists anyway as it was necessary for producing the master model. Thus it is merely necessary to pour out said individual spoon with the specific heat-resistant molding substance.

Alternatively, it is also possible to produce the heat-treatment model by using plaster as a key component, molding said plaster by enveloping the impression jigs of the master model. Using plaster as a key component is recommendable in particular with oblique heads to be fitted to implanted bolts and adapted to the direction of the teeth.

It is preferred that the heat-treatment model is made from an embedding substance fitted to a support element. The support element according to the invention will be described in detail below, it allows the distortion-free anchoring of the model anchors as well as of the embedding substance. This entails the particular advantage that the model anchors will be received in recesses of the support element. It is excluded that the position of the model anchors will change during the heat treatment step.

According to the invention, the superstructure is screwed to the heat-treatment model prior to the heat treatment. In order to avoid deviations in shape and/or dimensions it is possible to screw the superstructure to the heat-treatment model more or less tightly when fitting it to the heat-treatment model. Depending on the degree of inaccuracy of the casted superstructure, it must possibly be subjected to a heat treatment or a fitting treatment several times in succession.

In a further process step the annealed superstructure is provided with a facing according to the invention, e.g. with a ceramic material. Commonly said material is provided as a powder and it is applied to the superstructure, namely to the master model. The thus coated superstructure will be fired several times. According to the invention, the heat-treatment model is subjected to said firing step in order to exclude a new distortion or deviations in dimension of the superstructure. This is of particular advantage as the ceramic coatings distort and shrink during firing and thus, as the firing step is performed at a temperature near the melting point of the superstructure, can lead to a change of shape of the superstructure or the support frame.

According to the invention the problem is also solved by means of a support element for a metal frame of an implant-supported superstructure which comprises two tightly connected carrier plates arranged in parallel to each other and provided with recesses for the insertion of the model anchors.

The support element according to the invention thus results in a stable basic construction the shape of which is not or not noticeably modified under the influence of heat.

It is a particular advantage if the support element is made of a material the coefficient of thermal expansion of which is substantially equal to the coefficient of thermal expansion of an embedding substance for supporting the model anchors, to the coefficient of thermal expansion of the metal frame of the superstructure and/or to the coefficient of thermal expansion of a facing material for facing the superstructure. Due to the selected materials and the combination thereof thermal stress as well as stress from different coefficients of thermal expansion will be avoided. Distortion or deformation of the superstructure can thus be excluded.

It is particularly favorable if the two parallel carrier plates have a grid-like structure. Said grid-like structure allows a penetration or permeation of embedding substance, so that same is retained and "reinforced" by the carrier plates. This excludes cracking or deformation of the embedding substance during the heat treatment or when the superstructure is mounted. The mesh size of the grid of the upper carrier plate is preferred to be larger than the mesh size of the grid of the lower carrier plate. This supports the enclosure of the upper carrier plate by the embedding substance, while the lower carrier plate substantially retains the embedding substance and prevents it from flowing out.

It is preferred that the carrier plate is made of a non-scaling material or of a material not apt to scale; alloys of cobalt-chromium proved to be particularly advantageous. However, it is also possible to make the support element of ceramic materials.

According to the invention the support element can be produced in a resuable manner, wherein the embedding substance can e.g. be removed by sandblasting when the work is finished.

In order to facilitate the insertion of the model anchor it can be of advantage to provide the upper carrier plate with at least one recess of e.g. arch-like shape and following the shape of the jawbone. It is possible, however, to dimension the mesh size of the grid correspondingly or to produce individual recesses.

BRIEF DESCRIPTION OF THE DRAWINGS

Below the invention is described by way of examples with reference to the accompanying drawings of which.

DETAILED DESCRIPTION OF THE INVENTION

FIGS. 1 to 5 illustrate schematically the mode of procedure for producing a superstructure.

Figure 1:
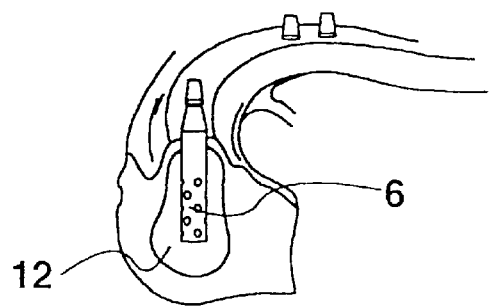
FIG. 1 shows a perspective illustration of part of a patient's lower jawbone.
Figure 2:
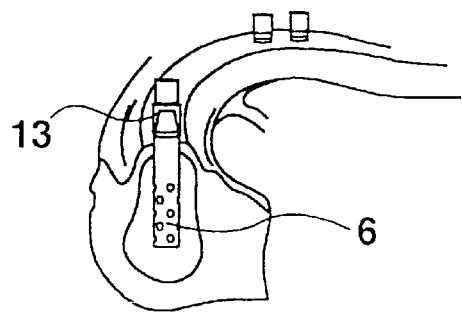
FIG. 2 shows an illustration similar to that of FIG. 1, with fitted transfer jigs.
Figure 3:
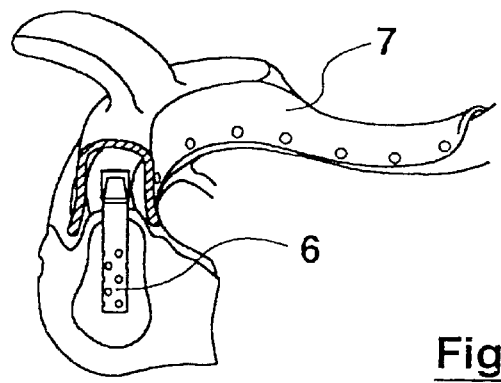
FIG. 3 shows an illustration similar to that of FIG. 2 with a fitted individual spoon.
Figure 4:
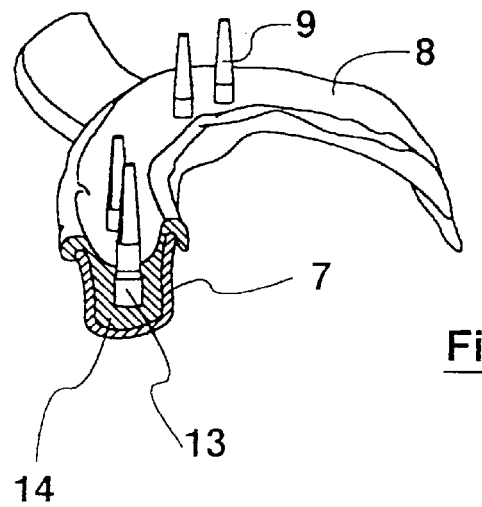
FIG. 4 shows a bottom view of an impression of the oral situation according to FIG. 3 and after the insertion of model implants.

FIG. 1 schematically illustrates the situation in a patient's mouth, in a jawbone 12 of a lower jaw there are fitted implant bolts 6. As shown in FIG. 2, transfer jigs 13 are screwed this way. As shown in FIG. 3 an impression is then taken by means of an individual spoon 7, with transfer jigs 13 being embedded in an impression material 14. FIG. 4 shows a bottom view of the finished impression 8, with model implants 9 being screwed into transfer jigs 13, the position and alignment of said model implants 9 corresponding to those of implant bolts 6.

Using impression 8 as shown in FIG. 4, a master model 10 is produced in conventional manner, with the model implants 9 being imbedded in master model 10. Using master model 10 a superstructure 1 or its support frame can be molded from wax and casted off.

Figure 6:
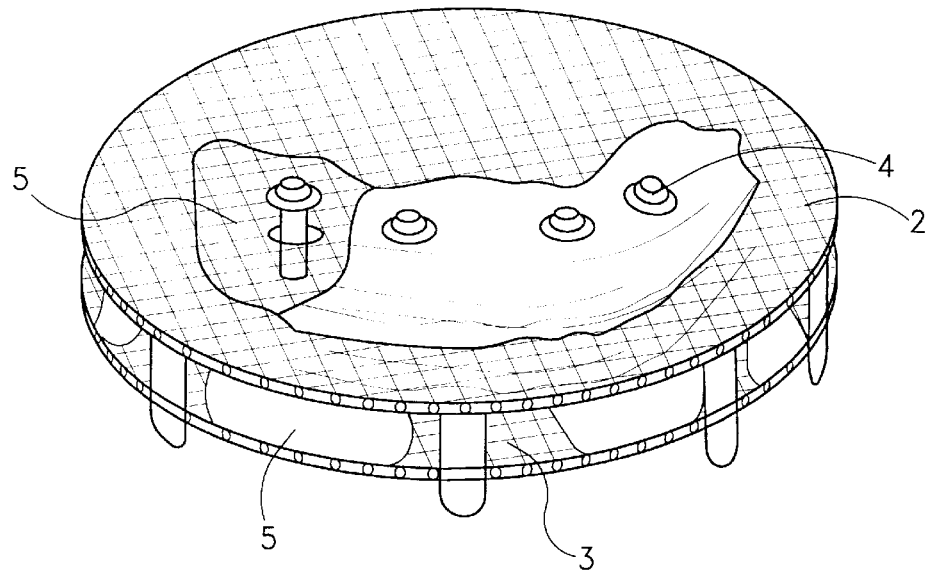
FIG. 6 shows a simplified perspective illustration of a heat-treatment model according to the invention using the support element according to the invention, an embedding substance being applied into which model anchors are inserted.

FIG. 6 shows an example of the heat-treatment model according to the invention. It comprises a support element composed of an upper carrier plate 2 and a lower carrier plate 3. As shown schematically, said two carrier plates are formed like grids or gratings.

Figure 5:
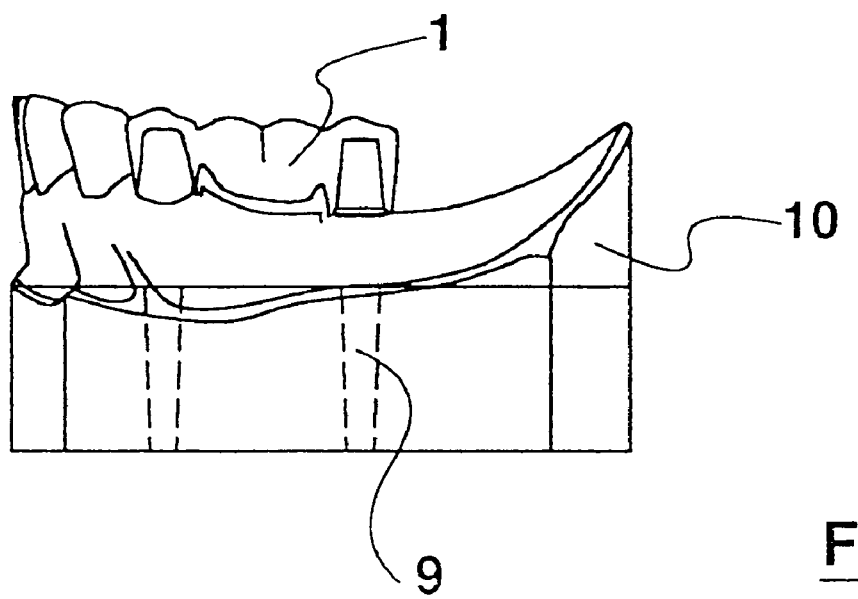
FIG. 5 shows a simplified illustration of a master model with inserted superstructure.

Using impression 8 of individual spoon 7 as shown in FIG. 4 there is produced a heat-treatment model by means of an embedding substance 5 applied on carrier plates 2, 3, the shape and the dimension of said heat-treatment model being similar to the situation in the patient's mouth (FIGS. 1 and 2) as well as to master model 10 (FIG. 5). In place of the model implants shown in FIG. 4 model anchors 4 are inserted, which extend through recesses of upper carrier plate 2.

It is evident from FIG. 6 that the embedding substance 5 will reach the intermediate space between the two carrier plates through upper carrier plate 2, so that the grid-like upper carrier plate 2 forms a "reinforcement" for embedding substance 5. This means that the latter is tightly anchored to the support element forming a reliable support for model anchors 4.

Figure 7:
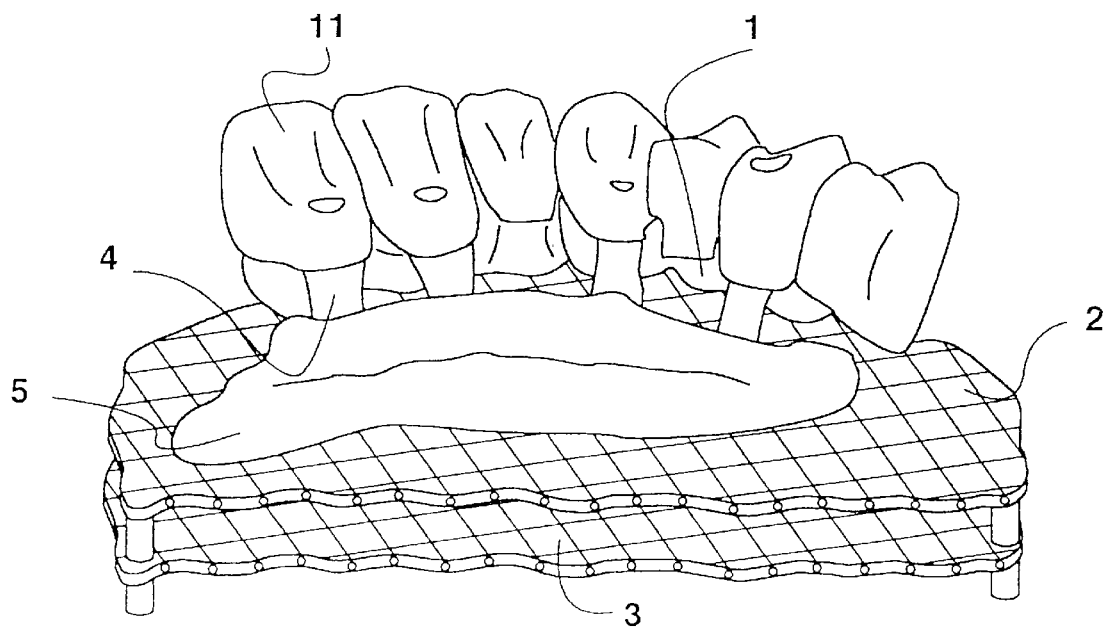
FIG. 7 shows a schematic backview of the heat-treatment model with the ceramic-faced superstructure fitted to the model anchors.

FIG. 7 shows a backview of the situation described in FIG. 6, with superstructure 1 being fitted in addition. To said superstructure facing material 11, e.g. ceramic material, can be applied.

Figure 9:
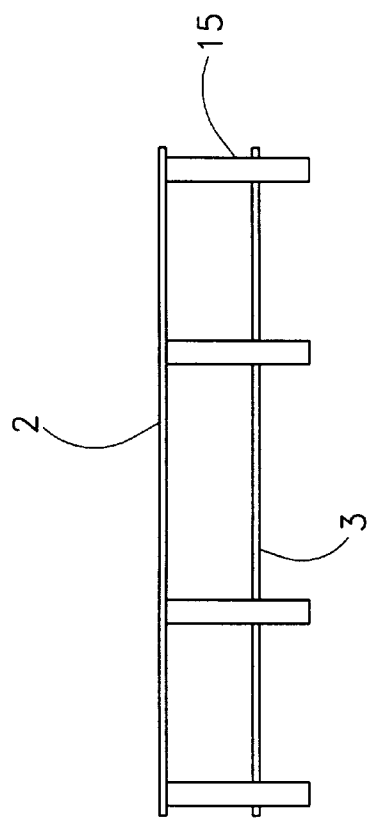
FIG. 9 shows a schematic side view of the support element shown in FIG. 8.
Figure 8:
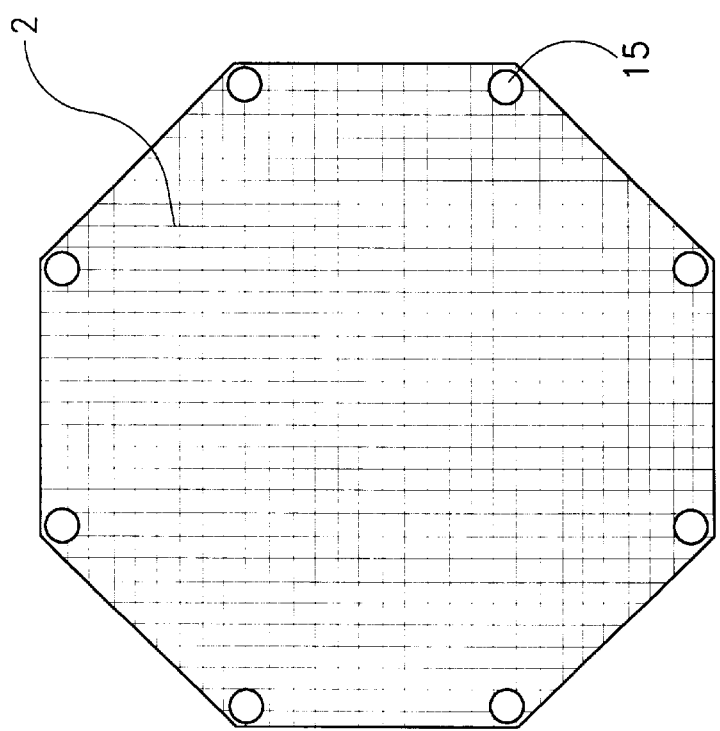
FIG. 8 shows a schematic top view of a further embodiment of the support element according to the invention.

FIGS. 8 and 9 show a further example of the support element according to the invention where same is designed as octagonal grid-shaped carrier plates. To said plates ribs 15 are mounted integrally which are to support carrier plates 2, 3 and contribute to the reinforcement of the support element.

Figure 10:
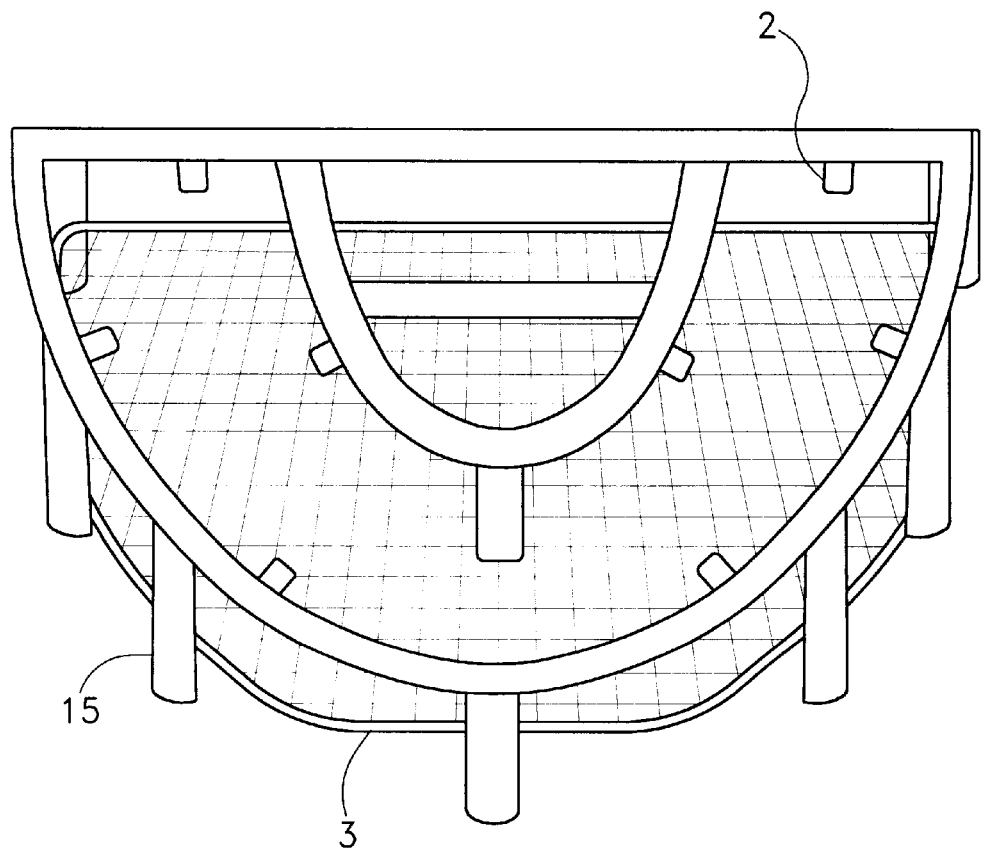
FIG. 10 shows a simplified perspective illustration of a further embodiment of the support element according to the invention.
Figure 11:
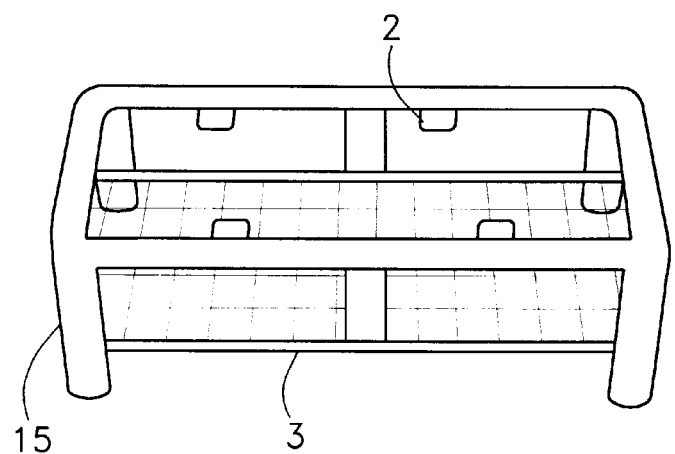
FIG. 11 shows a further simplified perspective illustration of the support element according to the invention.

FIGS. 10 and 11 show further examples of the support element according to the invention. From said figures it is clearly evident that the two carrier plates exhibit a most different mesh size. Lower carrier plate 3 has a very narrow mesh size, whereas upper carrier plate 2 is shaped like a very rough grid, the connection ribs of which were removed or omitted in part. With this embodiment it is no longer necessary to insert recesses for passing through model anchors to the upper grid plate, as their rough mesh size provides sufficient space for the model anchors. The upper carrier plate can be designated as retention grid.

The heat-treatment model according to the invention thus allows to align the superstructure in a direction ready for fitting and to subject it to a heat treatment in this alignment. This ensures the exact shape of the superstructure and it is also excluded that subsequent processing steps, e.g. firing for hardening a facing, will cause deformations of the superstructure.

The method according to the invention can also be used to make further preparations in dental medicine fit accurately, e.g. dental bridges.

In summary the following must be stated:

The invention relates to a method of producing an implant-supported superstructure, with a heat-treatment model being prepared subsequent to the production of a superstructure 1, which heat-treatment model is identical to a master model and/or the situation in a patient's mouth and on which a heat-treatment of the superstructure is performed in order to make it exactly fit on the master model.

What is claimed is:

1. A support element for a metal frame of an implant-supported superstructure that is to be placed in a person's mouth, comprising two tightly connected carrier plates arranged in parallel to one another and provided with recesses for inserting adjacent model anchors, the carrier plates sized to support the metal frame.

2. The support element according to claim 1, wherein the material of the support element has a coefficient of thermal expansion which is substantially equal to the coefficient of thermal expansion of an embedding substance for retaining the model anchors, to the coefficient of thermal expansion of the metal frame of said superstructure and to the coefficient of thermal expansion of the facing material for facing said superstructure.

3. The support element according to claim 1, wherein said carrier plates are of grid-like shape and the recesses extend across more than one grid.

4. The support element according to claim 3, wherein the carrier plates comprise an upper and lower plate, and wherein the mesh size of the grid of said upper carrier plate is larger than the mesh size of the grid of said lower carrier plate.

5. The support element according to claim 1, wherein the support element is made of non-scaling material.

6. The support element according to claim 1, wherein the support element comprises of an alloy free of precious metal and containing cobalt and chromium.

7. The support element according to claim 1, wherein the support element is reusable.

8. The support element according to claim 1, wherein the carrier plates comprise an upper and lower plate, and wherein said upper carrier plate is provided with at least one recess for inserting model anchors.

9. The support element according to claim 8, wherein the recess is of arch-like shape.

10. A method of producing an implant-supported superstructure, after implanting of implant bolts into a patient's mouth, comprising the steps of:

preparing an impression of the situation of the patient's mouth by means of an individual spoon;

inserting model implants into this impression;

preparing a master model from said impression;

forming a wax mold of said superstructure or its support frame;

casting off said wax mold from said superstructure or its support frame;

producing a heat-treatment model similar to the oral situation represented by said master model;

inserting model anchors corresponding to the model implants into the heat-treatment model;

fitting said casted superstructure or its support frame to the heat-treatment model; and heat-treating said model together with said superstructure or its support frame.

11. The method according to claim 10, wherein said producing of the heat-treatment model includes impressing an individual spoon.

12. The method according to claim 10, wherein said producing of the heat-treatment model includes using plaster as a key component.

13. The method according to claim 10, wherein said producing of the heat-treatment model includes applying an embedding substance on a support element for a metal frame of an implant-supported superstructure with two tightly connected carrier plates arranged in parallel to one another and provided with recesses for inserting model anchors.

14. The method according to claim 13, wherein said inserting of the model anchors includes positioning the model anchors into recesses in the support element.

15. The method according to claim 10, including the further step of screwing said superstructure or its support frame to the heat-treatment model.

16. The method according to claim 10, including the further step of deforming said superstructure or its support frame prior to being fitted to the heat-treatment model for removing deviations in at least one of the shape and dimensions.

17. The method according to claim 10, including the further step of annealing said superstructure or its support frame stress-relieved during the heat treatment step.

18. The method according to claim 10, including the further steps of mounting said superstructure or its support frame to the heat-treatment model after each application of a facing material; and heat-treating the superstructure or its support again, in order to avoid distortion.

19. An apparatus including a support element for use in heat treating an implant-supported superstructure that is fastened to a heat-treatment model for a dental superstructure, the model having model anchors corresponding to the implants, comprising first and second tightly connected carrier plates arranged in parallel to one another to form the support element, the fist plate having recesses located to allow passage of the anchors with the second plate being spaced close enough to the first plate to support the heat-treatment model during heat treating when the heat-treating model is placed on the support element.

20. An apparatus as defined in claim 19, wherein the support plates comprise grid structures.

21. An apparatus as defined in claim 20, further comprising the heat-treatment model, with the heat-treatment model being representative of an oral situation in a patient's mouth for which the superstructure is configured.

22. An apparatus as defined in claim 21, wherein the heat-treatment model is comprised of an embedding substance, a portion of which penetrates the grid of the first plate, the first plate having one or more model anchors extending therethrough and into the embedding substance.

23. An apparatus as defined in claim 22, wherein the material of the support element has a coefficient of thermal expansion which is substantially equal to a coefficient of thermal expansion of the embedding substance.

24. An apparatus as defined in claim 19 further comprising the superstructure or a support frame for the superstructure, with one of the superstructure or the support frame being screwed to the heat-treatment model.

25. An apparatus as defined in claim 24, wherein the superstructure or its support frame has been stress-relieved by annealing while screwed to the heat-treatment model.

26. An apparatus as defined in claim 24, further comprising a facing material applied to the superstructure, with the facing material and superstructure being annealed to relieve stress while the superstructure is screwed to the heat-treatment model.

27. An apparatus as defined in claim 26, wherein the material of the support element has a coefficient of thermal expansion which is substantially equal to the coefficient of thermal expansion of the frame of the superstructure and of the facing material.

28. An apparatus as defined in claim 19, wherein the material of the support element has a coefficient of thermal expansion which is substantially equal to a coefficient of thermal expansion of the heat-treatment model, and to a coefficient of thermal expansion of a metal frame of the superstructure.

29. An apparatus as defined in claim 19, wherein the recess has an arch-like shape following the shape of a person's jawbone.

\* \* \* \* \*

UNITED STATES PATENT AND TRADEMARK OFFICE
CERTIFICATE OF CORRECTION

PATENT NO.    : 6,022,215
DATED         : February 8, 2000
INVENTOR(S)   : Rainer Janousch It is certified that error appears in the above-identified patent and that said Letters Patent is hereby corrected as shown below:

<u>Column 5, claim 1,</u>
Line 59, after the word "frame", the following words should be added: -- , and at least one model anchor extending through one of the carrier plates --.

<u>Column 7, claim 19,</u>
Line 12, change "fist" to -- first --.

Signed and Sealed this

Nineteenth Day of March, 2002

Attest:

JAMES E. ROGAN
*Director of the United States Patent and Trademark Office*

*Attesting Officer*